United States Patent
Khasnis

(10) Patent No.: US 9,125,797 B2
(45) Date of Patent: Sep. 8, 2015

(54) PROGRAMMABLE SYSTEM WITH VISUAL INDICATION FOR MEDICINE CONSUMPTION

(75) Inventor: Himamshu Gopalakrishna Khasnis, Bangalore (IN)

(73) Assignee: Signalchip Innovations Pvt. Ltd., Bangalore (IN)

( * ) Notice: Subject to any disclaimer, the term of this patent is extended or adjusted under 35 U.S.C. 154(b) by 192 days.

(21) Appl. No.: 13/608,707

(22) Filed: Sep. 10, 2012

(65) Prior Publication Data
US 2013/0087469 A1 Apr. 11, 2013

(30) Foreign Application Priority Data
Oct. 5, 2011 (IN) .......................... 3452/CHE/2011

(51) Int. Cl.
| | |
|---|---|
| *G08B 1/00* | (2006.01) |
| *A61J 7/04* | (2006.01) |
| *A61J 1/03* | (2006.01) |
| *G06F 19/00* | (2011.01) |

(52) U.S. Cl.
CPC ................ *A61J 7/0409* (2013.01); *A61J 1/035* (2013.01); *A61J 1/1418* (2015.05); *A61J 7/0418* (2015.05); *A61J 7/0454* (2015.05); *A61J 2200/30* (2013.01); *A61J 2205/20* (2013.01); *A61J 2205/60* (2013.01); *G06F 19/3462* (2013.01)

(58) Field of Classification Search
USPC .................................................... 340/309.16
See application file for complete search history.

(56) References Cited

U.S. PATENT DOCUMENTS

| | | | |
|---|---|---|---|
| 5,412,372 A * | 5/1995 | Parkhurst et al. .......... 340/568.1 |
| 5,719,780 A | 2/1998 | Holmes et al. |
| 6,226,564 B1 | 5/2001 | Stuart |
| 6,335,692 B1 * | 1/2002 | Compton .................... 340/815.4 |
| 7,304,913 B2 * | 12/2007 | Niemiec et al. ................. 368/10 |
| 7,440,817 B2 | 10/2008 | Fu |
| 7,978,564 B2 | 7/2011 | De La Huerga |
| 8,193,918 B1 * | 6/2012 | Shavelsky et al. ........ 340/309.16 |
| 2001/0028308 A1 * | 10/2001 | De La Huerga ........... 340/573.1 |
| 2005/0110640 A1 * | 5/2005 | Chung ........................ 340/572.1 |
| 2005/0150897 A1 * | 7/2005 | Fabricius et al. ................. 221/2 |
| 2006/0086639 A1 * | 4/2006 | Priebe et al. ................... 206/528 |
| 2007/0194890 A1 * | 8/2007 | Brue ........................ 340/309.16 |
| 2008/0061965 A1 * | 3/2008 | Kuhns et al. .............. 340/539.22 |
| 2010/0000899 A1 * | 1/2010 | Burg et al. ................... 206/459.1 |
| 2010/0036681 A1 * | 2/2010 | Naik et al. ......................... 705/3 |
| 2012/0024889 A1 * | 2/2012 | Robertson et al. .............. 222/23 |

* cited by examiner

*Primary Examiner* — Naomi Small
(74) *Attorney, Agent, or Firm* — Rahman LLC

(57) ABSTRACT

A programmable system to visually indicate a predefined tablet to be consumed at a predefined time is provided. The programmable system includes a plurality of sections each corresponding to one of a plurality of tablets in a tablet strip, a wired interface or a wireless interface coupled to the plurality of sections. The wired interface or the wireless interface receives a set of instructions that include a set of sections and their corresponding times from a programming device. A memory stores the set of instructions. A timer tracks time and generates a message based on the set of instructions. A controller generates an electrical stimulus and communicates the electrical stimulus to a first section of the plurality of sections at a first time based on the set of instructions. The first section is modified visually at the first time in response to the electrical stimulus.

7 Claims, 19 Drawing Sheets

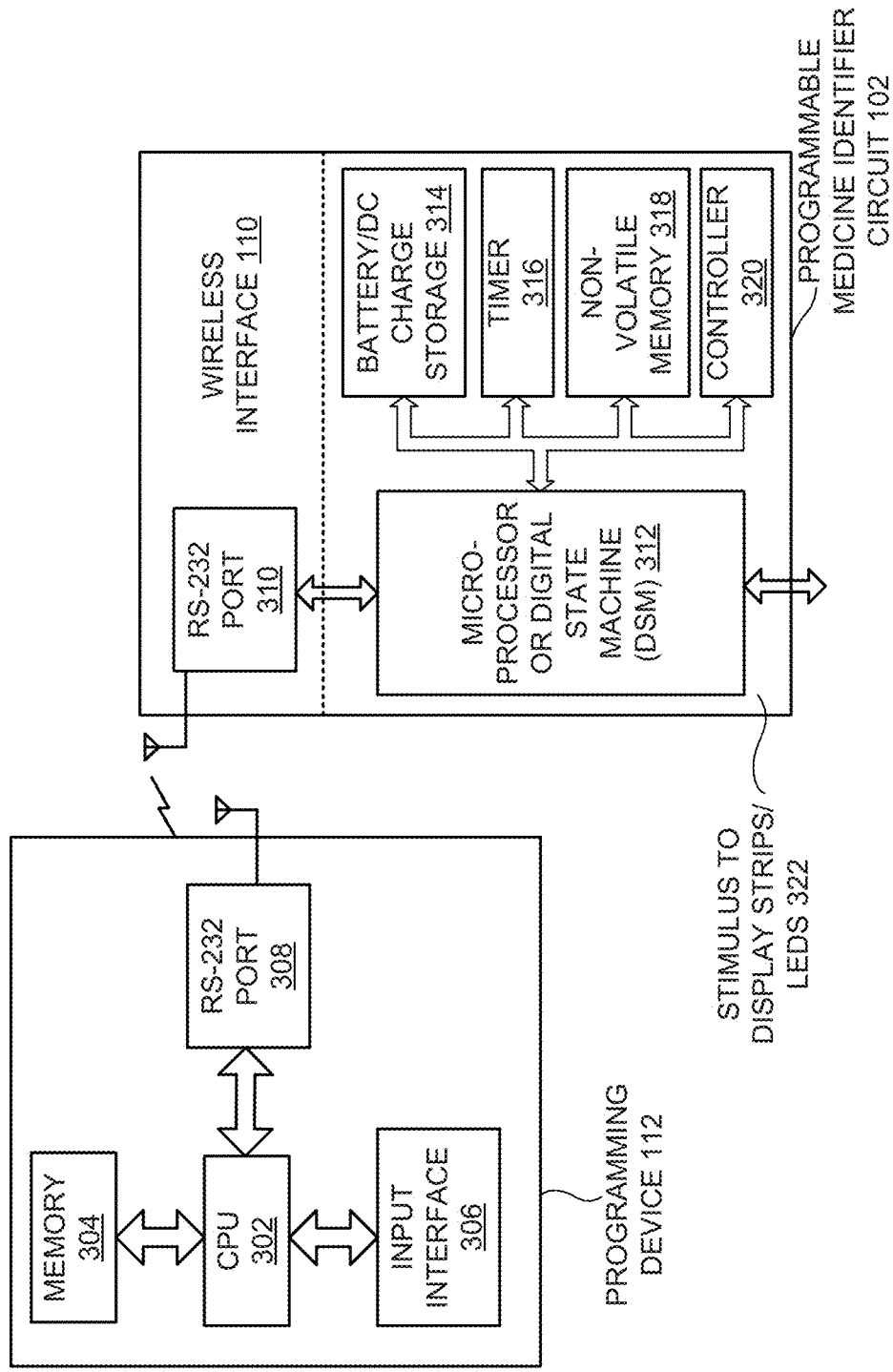

| Prescription Database 1404 | | | | Strip Database 1406 | | |
|---|---|---|---|---|---|---|
| Medicine type 1602 | Total pills to be consumed during treatment/regimen 1604 | Timing 1606 | Dosage in number of tablets 1608 | Number of Strips 1610 | Number of sub-systems per strip 1612 | Number of pills per sub-system 1614 | Sub-system ID 1616 |
| Amox | 10 | 8AM - 10AM | 1 | 1 | 1 | 10 | AAA1 |
| | | 8PM-10PM | 1 | | | | |
| Cetrizine | 4 | 8AM - 10AM | 1 | 1 | 4 | 1 | BBB1 |
| | | | | | | | BBB2 |
| | | | | | | | BBB3 |
| | | | | | | | BBB4 |
| Crocin | 9 | 8AM-10AM | 1 | 1 | 1 | 10 | CCC1 |
| | | 2PM-4PM | 1 | | | | |
| | | 8PM-10PM | 1 | | | | |
| Vitamin B | 30 | 8PM-10PM | 1/2 | 3 | 1 | 10 | DDD1 |
| | | | | | | | CCC2 |
| | | | | | | | CCC3 |

FIG. 16

PROGRAMMABLE SYSTEM WITH VISUAL INDICATION FOR MEDICINE CONSUMPTION

BACKGROUND

1. Technical Field

The embodiments herein generally relate to medicine consumption, and, more particularly to, programmable system with visual indication for medicine consumption.

2. Description of the Related Art

With the ongoing advances in medicine field, there are a number of medicines available not only for the treatment of specific ailments but also as nutritional supplements to improve on one's health. There may be a number of medicines that one needs to take during a day. Further, the present day medicines do appear in different colors, sizes, shape or package. Also, in developing countries, a large percentage of the population is illiterate and may not be comfortable with usage of medicines that are prescribed for consumption. Also, patients of advanced age or with limited abilities may find it difficult to identify the right medicines. In such cases, it is not uncommon that the patient ends up taking a wrong medicine or a wrong dosage of medicine at a wrong time. This may be disastrous for the patient's health and can call for medical emergencies. Thus, there remains a need for a system that allows a patient to consume an appropriate medicine.

SUMMARY

In view of the foregoing, an embodiment herein provides a programmable system to visually indicate a predefined tablet to be consumed at a predefined time. The programmable system includes a plurality of sections each corresponding to one of a plurality of tablets in a tablet strip, at least one of a wired interface or a wireless interface coupled to the plurality of sections. At least one of the wired interface or the wireless interface receives a set of instructions that include a set of sections and their corresponding times from a programming device. A memory that stores the set of instructions. A timer that tracks time and generates a message based on the set of instructions. A controller that controls the wired interface or the wireless interface, the memory and the timer, and generates an electrical stimulus and communicates the electrical stimulus to a first section of the plurality of sections at a first time based on the set of instructions. The first section is modified visually at the first time in response to the electrical stimulus.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 4 illustrates of a wireless communication between the programming device 112 of FIG. 1 and the programmable medicine identifier circuit embedded within the medicine strip of FIG. 1 according to an embodiment herein;

FIG. 16 is a table view of the prescription database 1404 and the medicine strip database of FIG. 14 of the paired gadget of FIG. 7 according to an embodiment herein;

DETAILED DESCRIPTION OF PREFERRED EMBODIMENTS

Figure 1:
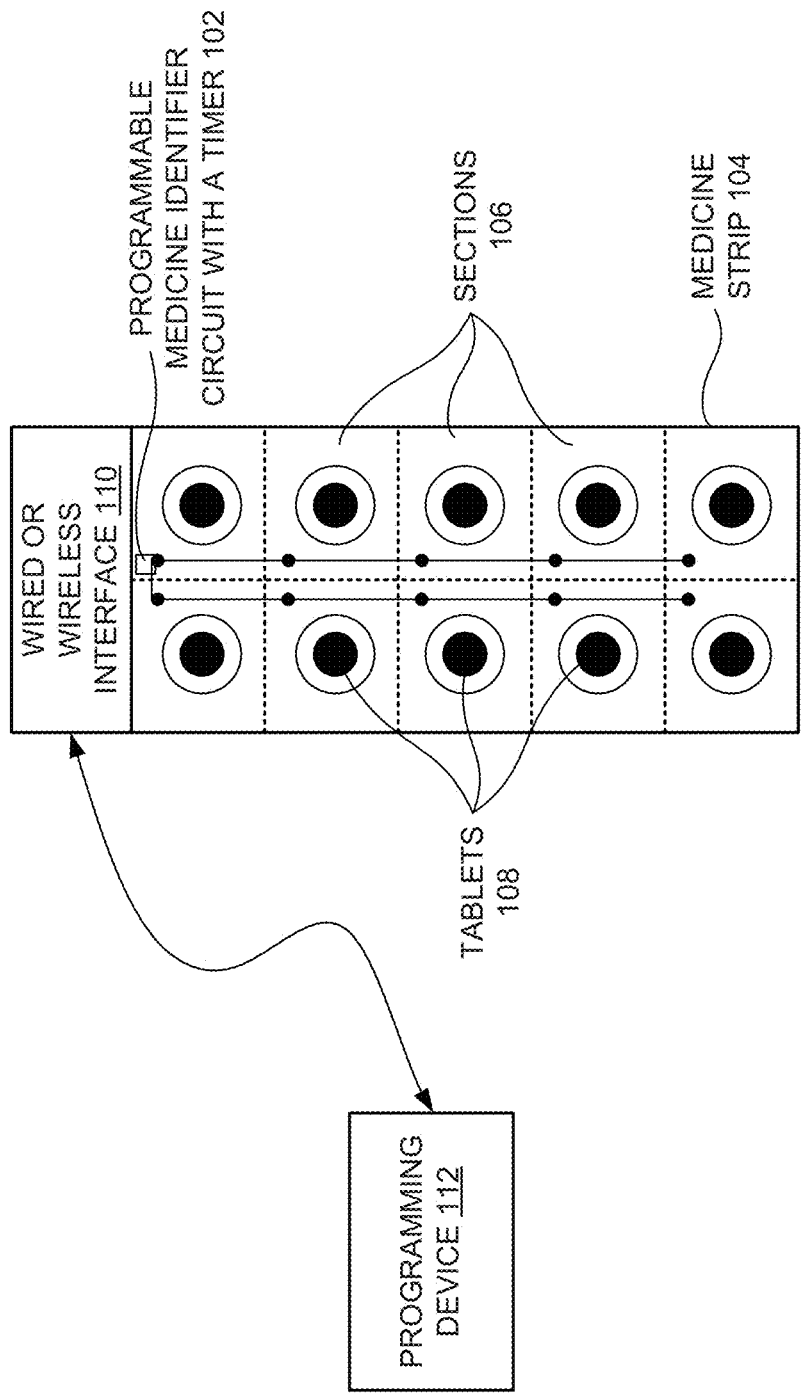
FIG. 1 illustrates a system view of a programmable medicine identifier circuit embedded within a medicine strip according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system that allows a patient to consume an appropriate medicine. The embodiments herein achieve this by providing a programmable system that visually indicates a predefined tablet to be consumed at a predefined time. Referring now to the drawings, and more particularly to FIG. 1 through FIG. 18, where similar reference characters denote corresponding features consistently throughout the figures, there are shown preferred embodiments.

FIG. 1 illustrates a system view 100 of a programmable medicine identifier circuit 102 embedded within a medicine strip 104 according to an embodiment herein. The system 100 includes the programmable medicine identifier circuit with a timer 102, the medicine strip 104, one or more sections 106 containing one or more tablets 108, at least one electric connecting point for each of the tablets 108, a wired interface or a wireless interface 110 connected to the medicine strip 104, and a programming device 112. The medicine identifier circuit 102 is linked to a packaging area for each of the tables 106 within the medicine strip 104 via wires or any other form of material that is capable of providing a visual indication.

The medicine identifier circuit 102 is programmed with one or more instructions via the wired or wireless interface 110 such that it provides a visual indication to a person a predefined tablet to be consumed at a predefined time. The wired interface or a wireless interface 110 is coupled to the one or more sections. The wired interface or the wireless interface 110 processes a set of instructions from the programming device 112. The instructions may include a set of sections and their corresponding times. The programmable medicine identifier circuit 102 further includes a low capacity battery that is embedded within the medicine strip 104 itself. The medicine strip 104 further includes an antenna or a coil that extracts energy based on an electromagnetic power scavenging mechanism. The medicine strip 104 may further include an embedded capacitor that stores charge based on the energy. A battery may be embedded within the medicine strip 104 itself.

Further, each of the sections 106 encloses not more than one tablet. The medicine strip 104 includes a receiver (not shown in FIG. 1) that obtains a stimulus from an external device indicating at least one of the sections corresponding to a prescription information stored on the external device, and a visual identification means that changes a visual appearance of the at least one of the sections 106 by at least one of changing a colour of the at least one of the sections 106 at least in part or by emitting light from the at least one of the sections 106 at least in part.

Figure 2:
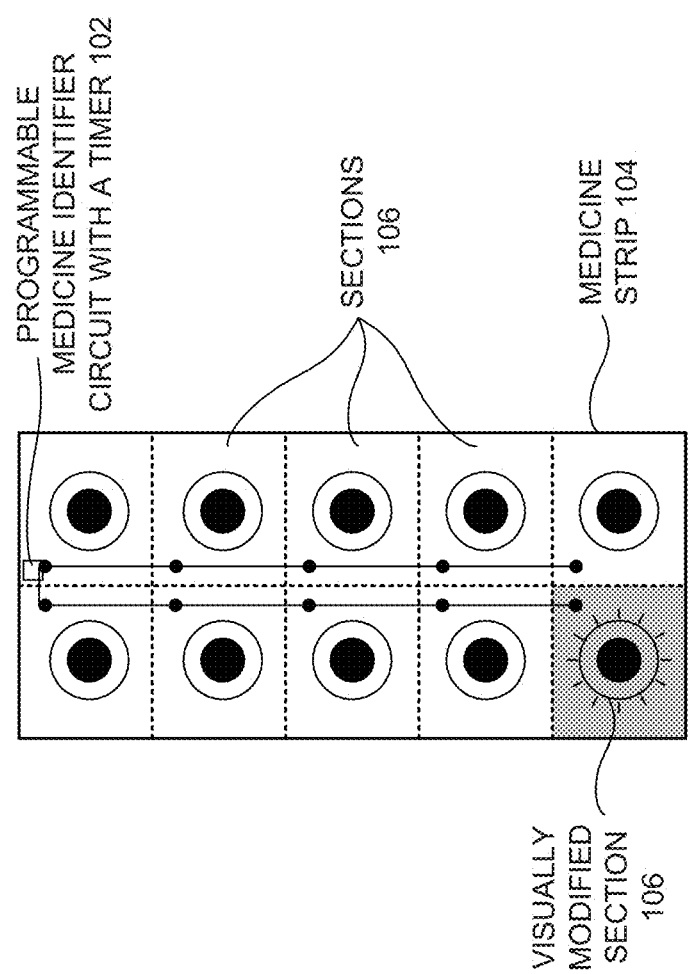
FIG. 2 illustrates a representation of at least one section of the medicine strip 104 of FIG. 1 that is visually modified according to an embodiment herein.

With reference to FIG. 1, FIG. 2 illustrates a representation of at least one section 106 of the medicine strip 104 of FIG. 1 that is visually modified according to an embodiment herein. The instructions trigger communication of an electronic stimulus to a first section 202 of one or more sections 106 at a first time. The first section is modified visually at the first time in response to the electronic stimulus. In one embodiment, the electronic stimulus changes the visual appearance of the first section 202 corresponding to a tablet. In one embodiment, the first section is partially modified visually in proportion to the dosage information corresponding to the first section. In another embodiment, the first section is modified visually by changing a colour of the first section at least in part. In yet another embodiment, the first section is modified visually by emitting light from the first section at least in part. The instructions include a dosage information and a consumption time information for each of the tablets.

Figure 3:
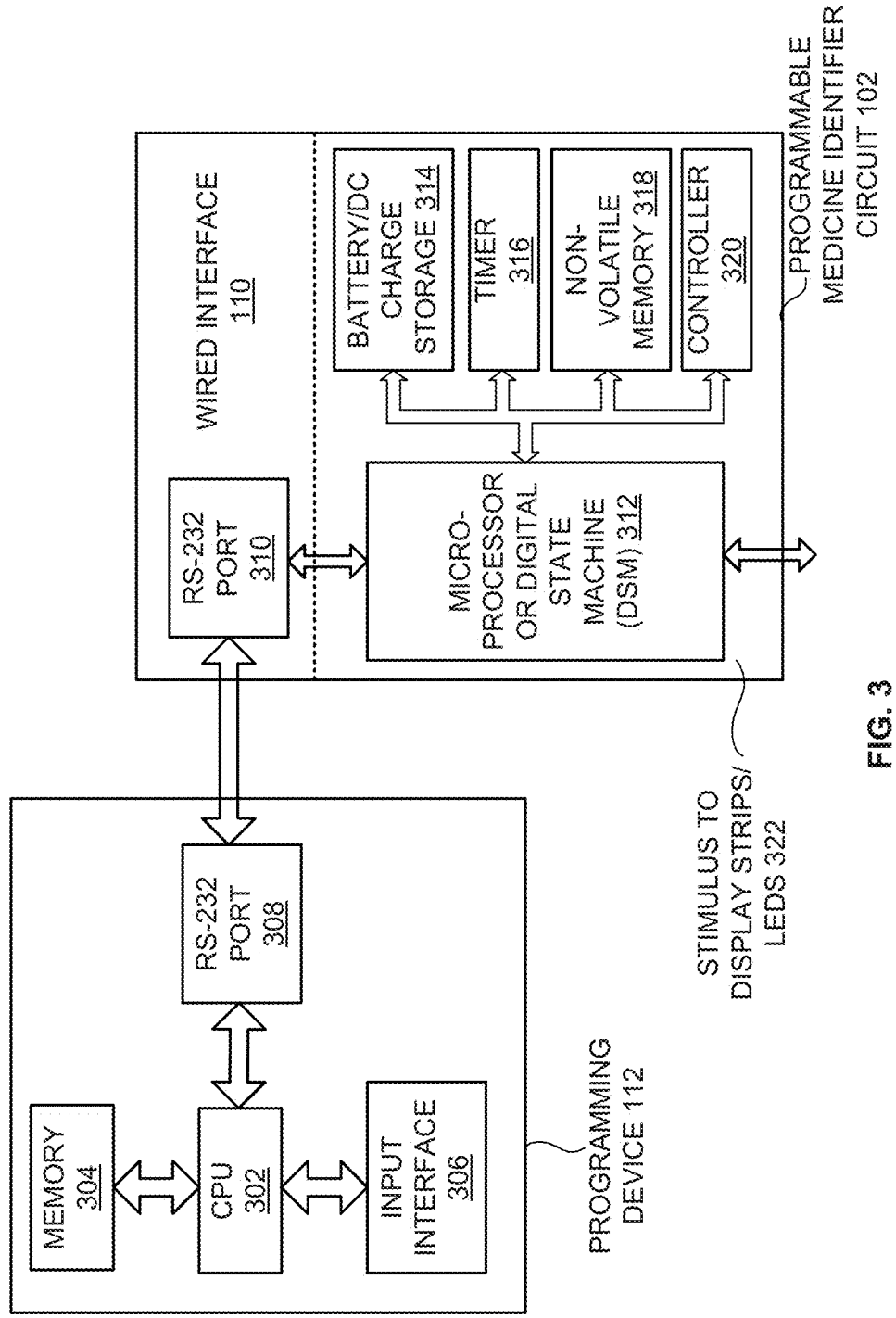
FIG. 3 illustrates an example of a wired communication between the programming device of FIG. 1 and the programmable medicine identifier circuit embedded within the medicine strip of FIG. 1 according to an embodiment herein.

FIG. 3 illustrates an example of a wired communication between the programming device 112 of FIG. 1 and the programmable medicine identifier circuit 102 embedded within the medicine strip 104 of FIG. 1 according to an embodiment herein. The programming device 112 includes a Central Processing Unit 302, a memory 304, an input interface 306, and a RS-232 port 308. The wired interface includes a RS 232 port 310. The programmable medicine identifier circuit 102 includes, a microprocessor or a digital state machine (DSM) 312, a battery/DC charge storage 314, a timer 316, a non-volatile memory 318, a controller 320, and a stimulus to display medicine strips/Light Emitting Diodes (LEDs) 322.

The memory 328 stores the set of instructions. The timer 316 tracks time and generates a message based on the set of instructions. The controller 320 controls the at least one of a wired interface or a wireless interface 110, the memory 328, and the timer 316 and generates an electrical stimulus and communicates the electrical stimulus to a first section of the plurality of sections 106 at a first time based on the set of instructions.

With reference to FIG. 3, FIG. 4 illustrates of a wireless communication between the programming device 112 of FIG. 1 and the programmable medicine identifier circuit 102 embedded within the medicine strip 104 of FIG. 1 according to an embodiment herein. The wireless interface and the programming device 112 may include a RF port instead of a RS 232 port.

The programmed data is processed by the Micro processor 312 of FIG. 3 and FIG. 4 that controls the operation of the programmable medicine identifier circuit 102. The processed data is stored on a non-volatile memory 318. The timer 316 counts time and generate interrupts or messages to a controller (not shown in FIGS.) at the appropriate time instants. The controller in-turn generates the appropriate input stimulus 320 for the tablets 102 which need to be visually differentiated (e.g., section 202 of FIG. 2).

In one embodiment, the sections of each tablet 108 include a ThermoChronic or a ElectroChronic label which ensures that they are isolated from other tablets on the medicine strip 104. This label is capable of changing its colour when an applied temperature and/or voltage are changed. Further, the change in the temperature and/or voltage of the label is achieved by the electronic stimulus applied by the controller (not shown in FIGS.).

In one embodiment a small LED 320 may be embedded on each of the sections 106 of the medicine strip 104. Once an electronic stimulus from the controller is received by the LED 320, the LED 320 glows identifying an appropriate tablet 108 to be consumed.

In one embodiment, the power to the programmable medicine identifier circuit 102 may be provided by the battery/DC charge storage 314 that can provide power through the duration of the consumption of the medicine/tablet. In another embodiment, the programmable medicine identifier circuit 102 can also be powered by an electromagnetic scavenging mechanism where electromagnetic waves in the vicinity of the medicine strip 104 are converted into a DC power, regulated and stored on an on-chip/printed capacitor.

Figure 5A:
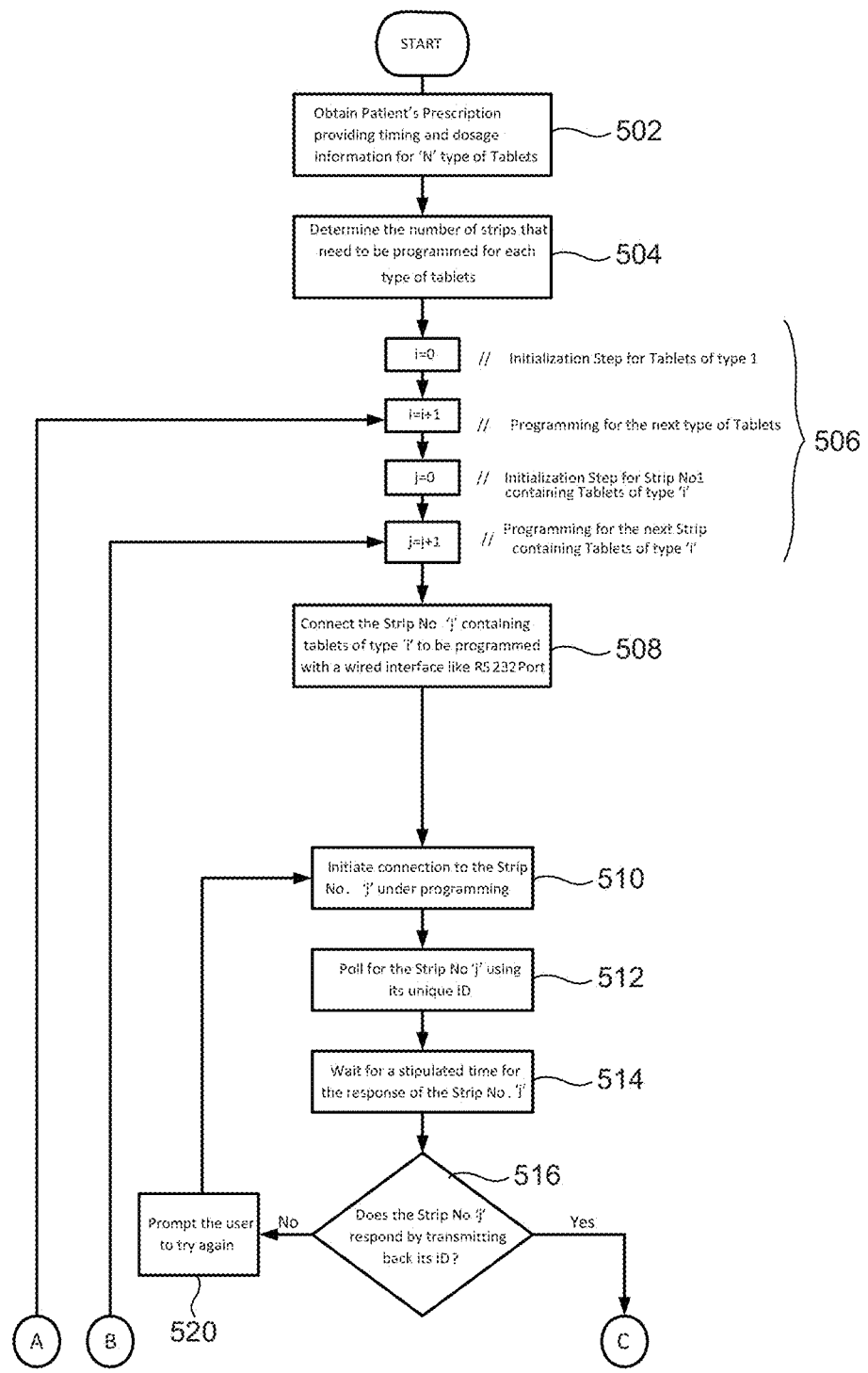
FIG. 5A through FIG. 5B is a flow diagram illustrating a method of programming one or more medicine strips using the programmable device of FIG. 1 according to an embodiment herein.
Figure 5B:
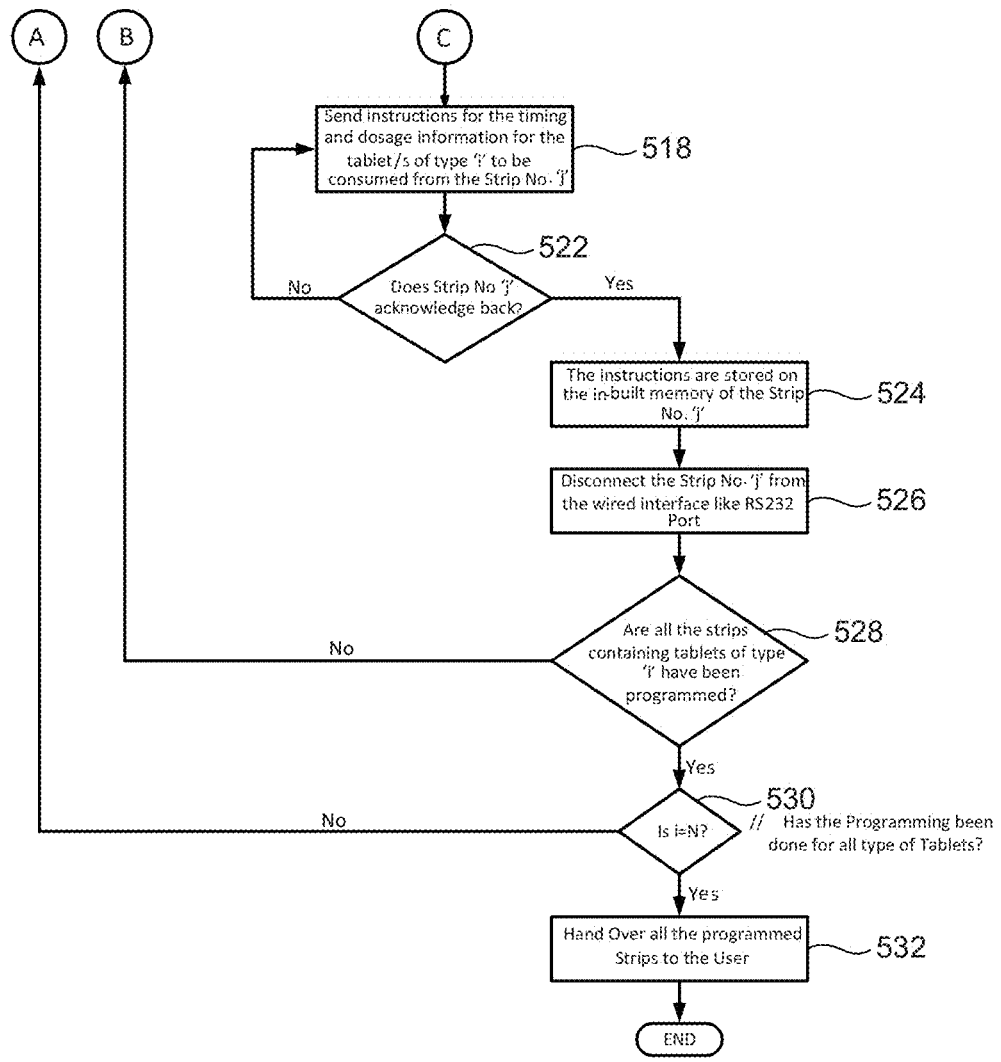

FIG. 5A through FIG. 5B is a flow diagram illustrating a method of programming one or more medicine strips or one or more guide cards using the programmable device 112 of FIG. 1 according to an embodiment herein. In one embodiment, a guide card does not contain tablets. A retailer can program all one or more medicine strips 104 using the programming device 112 (e.g., using a personal computer, or any computing device) etc. In step 502, the retailer obtains a prescription of a patient and goes through the timing and dosage information for 'N' type of prescribed tablets. In step 504, total number of medicine strips to be dispensed for each type of the prescribed tablets is calculated. Alternately, the prescription may be in a predefined electronic format provided by a physicist to a retailer by physically transporting to the retailer or through a communication network. In step 506, variables are initialized such as 'i' is set to zero (initialization step for tablets of type 1), i=i+1 for programming the next type of tablet, j=0—an initialization step for medicine strip 1 containing tablets of type 'i', j=j+1—programming a next medicine strip for tablet type 'i'.

The programming device 112 includes application software that runs through a list of tablets and prompts the retailer to program the medicine strips 104. The retailer then may start to program the medicine strips for each type of the prescribed tablets. In step 508, for every strip that needs to be programmed, it is first connected to a wired interface like an RS-232 port or to a wireless interface (e.g., RF port). The programming device 112 in-turn establishes a connection with the medicine strip 104. In step 510, a connection to the medicine strip 'j' is initiated.

In step 512, polling is performed for the medicine strip 'j' based on its unique ID. In step 514, a response indicating a stimulated time is received from the medicine strip 'j'. In step 516, it is checked whether the medicine strip 'j' responds by transmitting its unique ID. If the medicine strip 'j' responds by transmitting its unique ID, then instructions for the timing and dosage information for the tablets type 'i' for the medicine strip 'j' are sent in step 518. Else (if No), then user is prompted to try again at step 520 and step 510 is repeated. In step 522, it is checked whether the medicine strip 'j' acknowledges back once identified with its unique ID. If the medicine strip 'j' acknowledges back once identified with its unique ID, the instructions are stored on a memory (e.g., the memory 318 of FIG. 3 and FIG. 4) of the medicine strip 'j' in step 524. Else (if No), step 518 is repeated.

In step 526, the medicine strip 'j' is disconnected from the wired interface or the wireless interface. In step 528, it is checked whether all the medicine strips 'j' containing the tablet type 'i' have been programmed. If all the medicine strips 'j' containing the tablet type 'i' have been programmed, then it is checked whether "i=N" in step 530. Else (if No), then step 506 is repeated where j is incremented by 1 (e.g., j=j+1). If "i=N", then the medicine strips 'j' are handed over to the user in step 532. Else (if No), then step 506 is repeated where 'i' is incremented by 1 (e.g., i=i+1).

Figure 6:
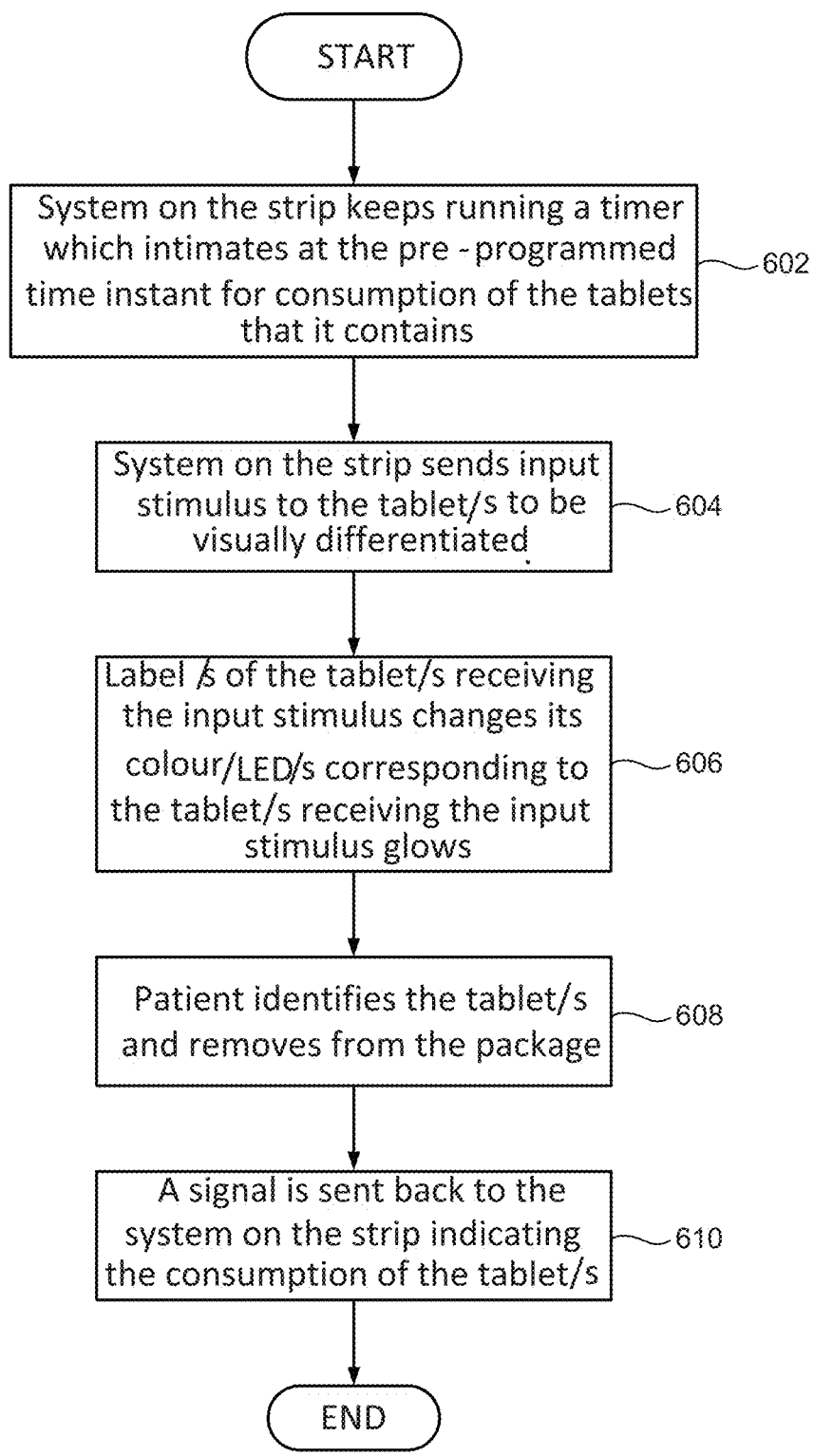
FIG. 6 is a flow diagram illustrating a method of programming individual tablets within a medicine strip to visually differentiate from others according to an embodiment herein.

FIG. 6 is a flow diagram illustrating a method of programming individual tablets within a medicine strip to visually differentiate from others according to an embodiment herein. In step 602, the medicine identifier circuit 102 keeps running a timer that intimates at a pre-programmed time instant for the consumption of tablets contained in the medicine strip 104. In step 604, an input stimulus (e.g., an electronic stimulus) is sent to the first section 106 of the tablet 108 by the medicine identifier circuit 102 to be visually differentiated. In step 606, the first section 106 of the tablet 108 receives the electronic stimulus and changes the colour (e.g., via LED) corresponding to the tablet and the stimulus glows. In step 608, the tablet from the corresponding section is identified based on the stimulus glow and is removed from the medicine strip 104 by a patient who needs to consume that tablet. In step 610, a signal is sent back to the medicine identifier circuit 102 indicating that the tablet is removed from the corresponding section and is consumed by the patient.

Figure 7:
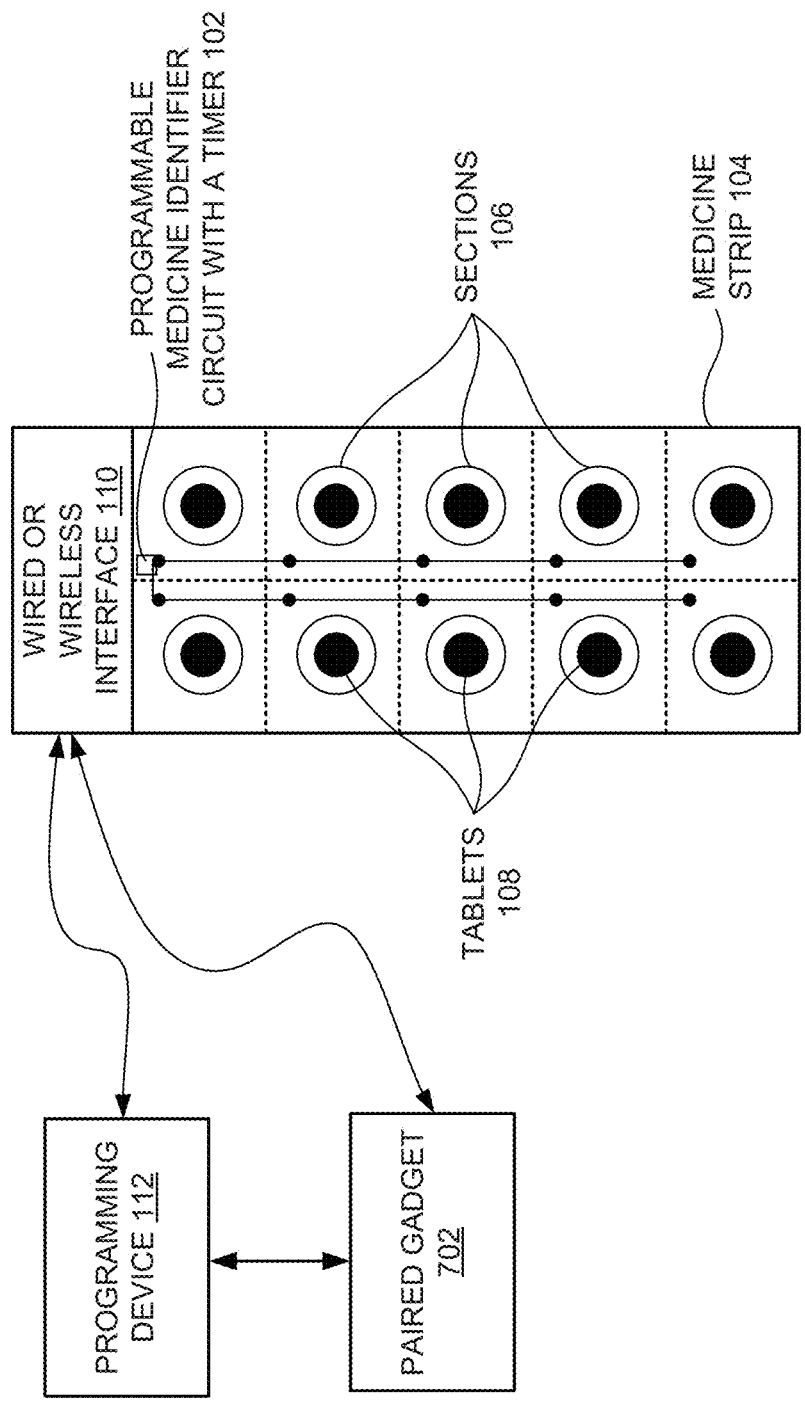
FIG. 7 is a block diagram illustrating a method of programming a paired gadget and the medicine strip using the programming device of FIG. 1 according to an embodiment herein.

FIG. 7 is a block diagram illustrating a method of programming a paired gadget 702 and the medicine strip 104 using the programming device 112 of FIG. 1 according to an embodiment herein. The medicine strip 104 includes the medicine identifier circuit 102 that uniquely identifies the tablet within the sections. The medicine strip 104 along with the medicine identifier circuit 102 is connected to the wired interface or the wireless interface 110 to be in communication with the paired gadget 702. The timing is run in the paired gadget 702. The retailer programs the paired gadget 702 with the prescription dosage and timing of consuming an appropriate tablet. At an appropriate time, when the paired gadget 702 is connected to the medicine strip 104 either through a wired or a wireless interface 110, the paired gadget 702 uses the stored identifier to send appropriate instructions to the medicine strip 104 to create a visually distinguishable area on the one or more sections that correspond to a particular tablet which needs to be consumed. For example, the paired gadget 702 may also be a mobile communication device.

Figure 8:
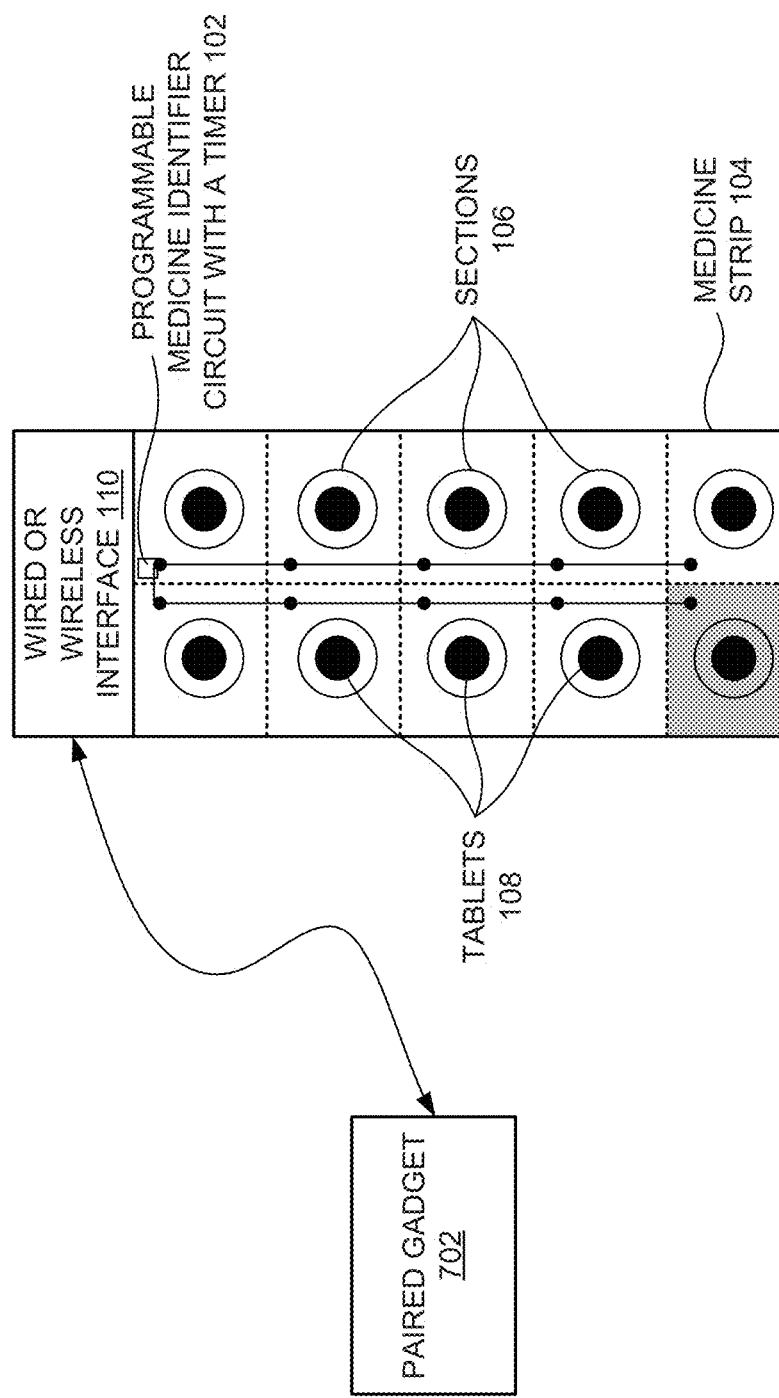
FIG. 8 is block diagram of the paired gadget of FIG. 7 used for assisting the medicine identifier circuit having a unique identifier on the medicine strip of FIG. 1 to visually indicate a predefined tablet to be consumed at a predefined time according to an embodiment herein.

FIG. 8 is block diagram of the paired gadget 702 of FIG. 7 used for assisting the medicine identifier circuit 102 having a unique identifier 802 on the medicine strip 104 of FIG. 1 to visually indicate a predefined tablet to be consumed at a predefined time according to an embodiment herein. The paired gadget 702 (e.g., the mobile communication device) includes a client application software (not shown in FIG.) that obtains an input from the retailer through a standard device-human interfaces (e.g. keypad/touch screen) or mobile-machine interfaces (e.g., Bluetooth technology, serial port, etc).

The mobile communication device enabled with the client application software is capable of communicating with the medicine identifier circuit 102 in the medicine strip 104 through Near Field Communication (NFC) or RFID mechanisms. In one embodiment, the medicine identifier circuit 102 has an inbuilt NFC/RFID transmission and reception capabilities and contain unique identification code encoded onto them during manufacturing. This code or a corresponding text is also printed on the medicine strip 104.

Figure 9:
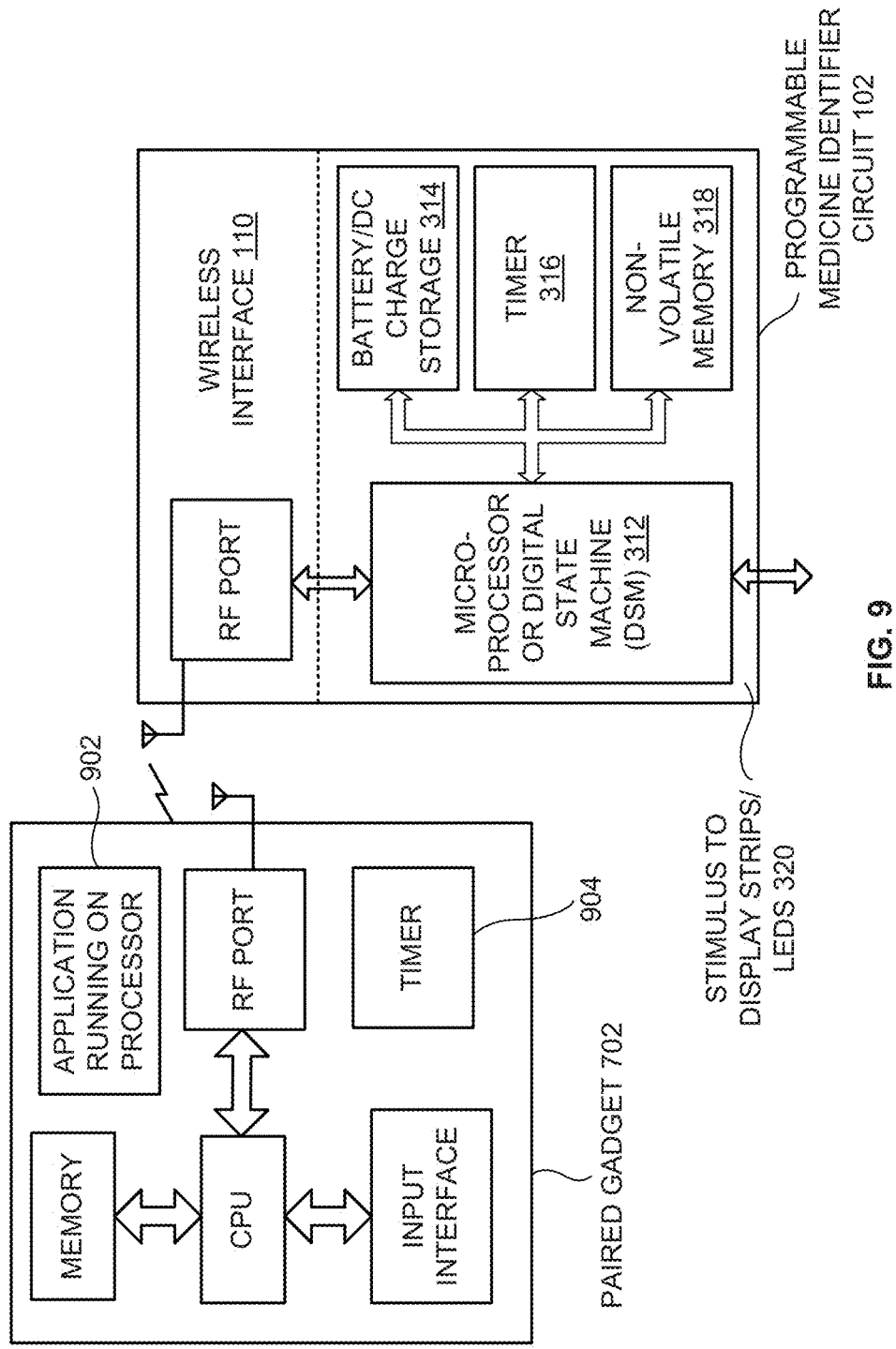
FIG. 9 is a block diagram of the paired gadget of FIG. 7 communicating with the medicine identifier circuit in the medicine strip of FIG. 1 according to an embodiment herein.

With reference to FIG. 8, FIG. 9 is a block diagram of the paired gadget 702 of FIG. 7 communicating with the medicine identifier circuit 102 in the medicine strip 104 of FIG. 1 according to an embodiment herein. In one embodiment, the retailer launches the client application software 902 and enters the details of the time and dosage of the medicines as per the prescription of the patient. Alternately, the prescription could be stored in an electronic form and automatically entered into the mobile communication device through a physical storage medium attached to it or through a paired personal computer or even directly from a communication network. Then the unique IDs 802 in the medicine strip 104 to the patient are paired with the entries in prescription already entered into mobile communication device.

This is done by a step in the client application software where through the prompting of the retailer, the client application software enters a "pairing mode" for each prescription entry. The retailer brings the corresponding the medicine strip 104 near the mobile communication device where the mobile communication device (e.g., the paired gadget reads the identifier 802 of the medicine strip 104 and displays a corresponding text on the screen. The retailer validates this with the printed text on the medicine strip 104 and confirms the entry through another prompt to the client application software. The complete prescription is thus paired with the client application software which stores all the details into memory.

In one embodiment, the client application software then runs in the mobile communication device either in a background mode or in a front mode and starts using the internal timing mechanisms of the mobile operating system to alert at appropriate time instants as per the prescription. At an appropriate instant, the client application software alarms to remind the patient. The patient then brings the mobile communication device in the vicinity of the medicine strip 104 and prompts the mobile communication device to enter an "identification" mode. In this mode the client application software again launches a communication protocol with the corresponding tablet on the medicine strip that needs to be consumed at that particular time.

For example, the application on the paired gadget 702 keeps running a timer 904 which intimates at the pre-programmed time instant of one or more types of tablets to be consumed. Once this time interrupt is received (it can be in the form of an audio alarm), the user brings the paired gadget close to the medicine strips. The paired gadget 702 then identifies the tablets which need to be consumed. It then finds the unique ID of the corresponding medicine strip which contains the tablet/s to be consumed. The paired gadget then initiates a connection to the medicine strip. It polls for the right strip by transmitting its unique ID. If the medicine strip corresponding to the transmitted unique ID is within the vicinity of the paired gadget 702, it acknowledges by transmitting back its unique ID and a connection is setup between the paired gadget 702 and the identified strip.

If there is no response from the medicine strip, the user may get an error message on the display of his/her paired gadget requesting to bring the paired gadget 702 closer to the medicine strip. The user can choose to bring the paired gadget 702 closer to the medicine strip and re-establish the connection between the paired gadget 702 and the medicine strip or he/she can skip and go to the programming of the next strip.

Once a connection between the paired gadget 702 and the medicine strip has been established, the paired gadget 702 transmits further instructions on the location of the tablet/s which need to be visually differentiated as per the information stored on the paired gadget 702. Upon receiving these instructions, the medicine strip acknowledges. The medicine identifier circuit 102 sends electronic stimulus to the tablet/s which need to be visually illuminated. The sections of the tablets that receives the input stimulus changes its colour (or LEDs corresponding to the tablets receiving the input stimulus glows) and allows the patient identify the correct tablets to be consumed. If there are more than one type of tablets to be consumed at a given instant, then the medicine strips containing the tablets become visually distinguishable and the patient can proceed with the right medicine for consumption.

Figure 10:
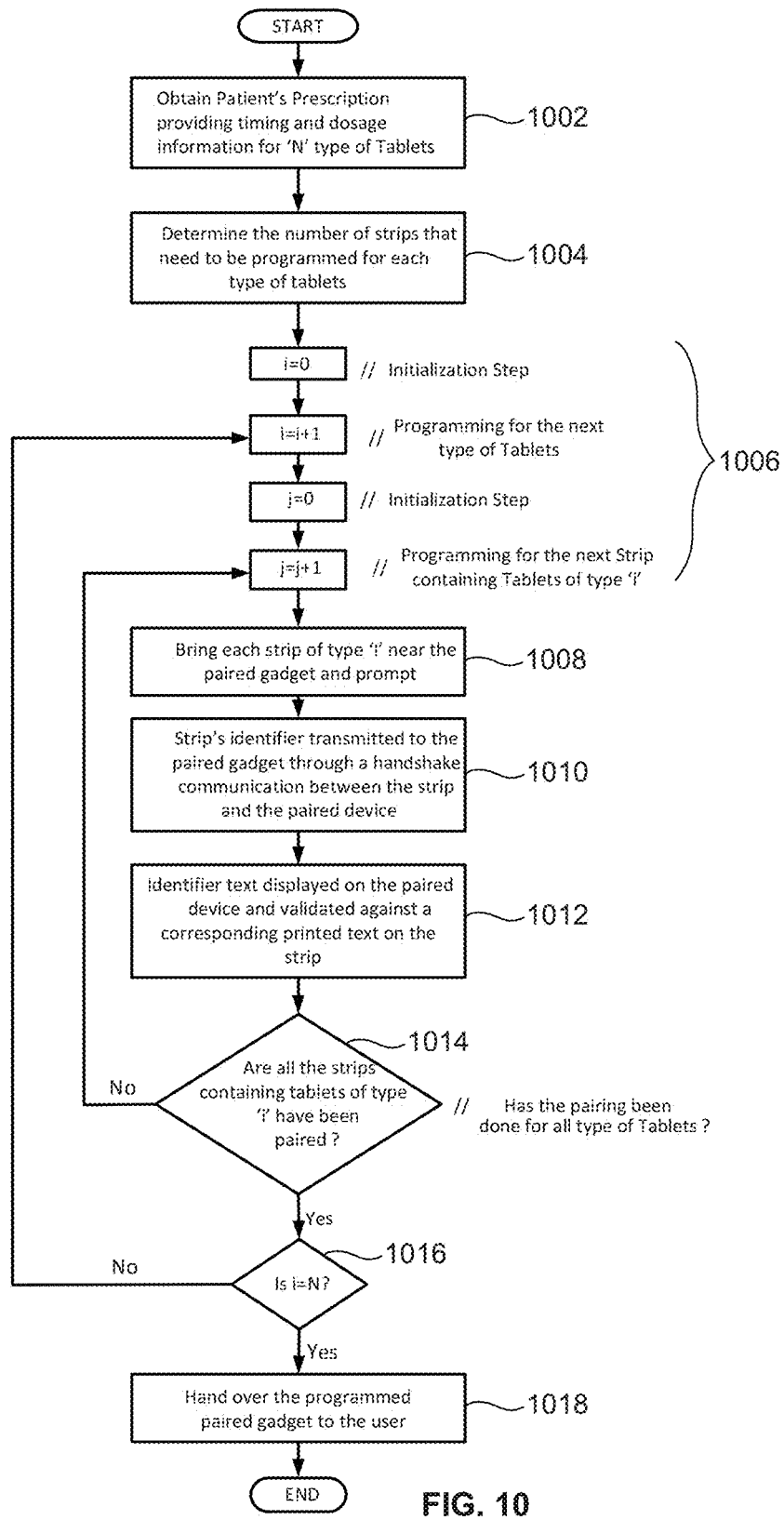
FIG. 10 is a flow diagram illustrating a method of pairing the medicine strips with the paired gadget of FIG. 7 according to the embodiment herein.

FIG. 10 is a flow diagram illustrating a method of pairing the medicine strips with the paired gadget 702 of FIG. 7 according to the embodiment herein. In step 1002, the retailer obtains the patient's prescription that indicates timing and dosage information for 'N' type of tablets. In step 1004, the retailer determines the number of medicine strips that need to be programmed for each type of tablet. In step 1006, one or more variables are initialized such as 'i' is set to zero (initialization step for tablets of type 1), i=i+1 for programming the next type of tablet, j=0—an initialization step for medicine strip 1 containing tablets of type 'i', j=j+1—programming a next medicine strip for tablet type 'i'. In step 1008, the retailer bring each strip of type 'i' near the paired gadget 702 to prompt.

In step 1010, a unique identifier of each medicine strip is transmitted to the paired gadget 702 through a hand shake communication between the medicine strip 104 and the paired gadget 702. In step 1012, the identifier text is displayed on the paired gadget 702 and validated with the corresponding printed text on the medicine strip. In step 1014, it is checked if all the medicine strips containing tablets of type 'i' have been paired. If all the medicine strips containing tablets of type 'i' have been paired, it is checked whether "i=N" in step 1016. Else (if No), then step 1006 is repeated by incrementing 'j' by 1 (i.e., j=j+1), where programming is performed for the next medicine strip of the tablet type 'i'. If "i=N", then the programmed paired gadget 702 is handed over to the user. Else (if No), step 1006 is repeated where 'i' is incremented by 1.

Figure 11A:
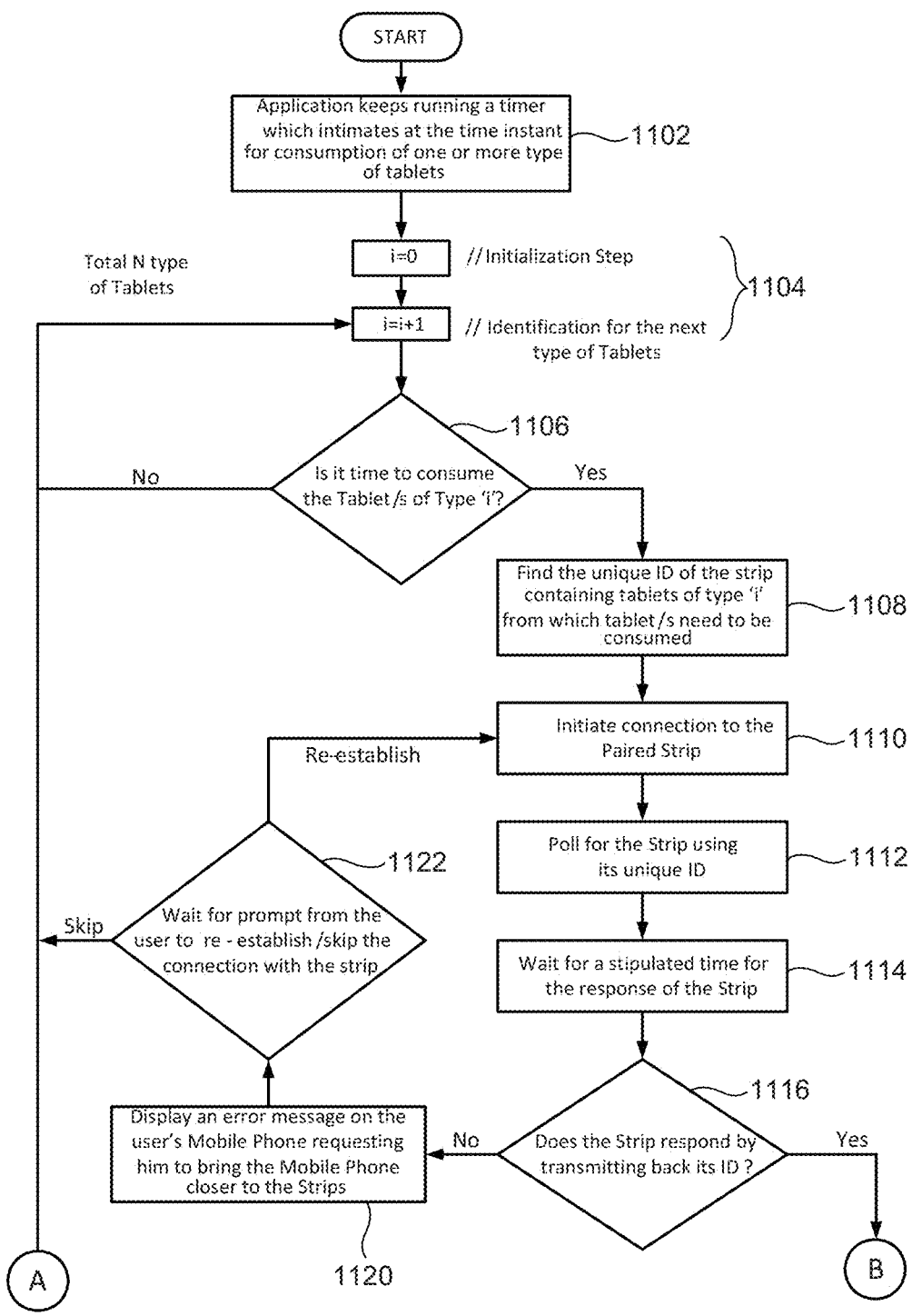
FIG. 11A through FIG. 11B is a flow diagram illustrating a method of using the medicine strip and the individual sections containing the corresponding tablets of FIG. 1 with the paired gadget of FIG. 7 according to an embodiment herein.
Figure 11B:
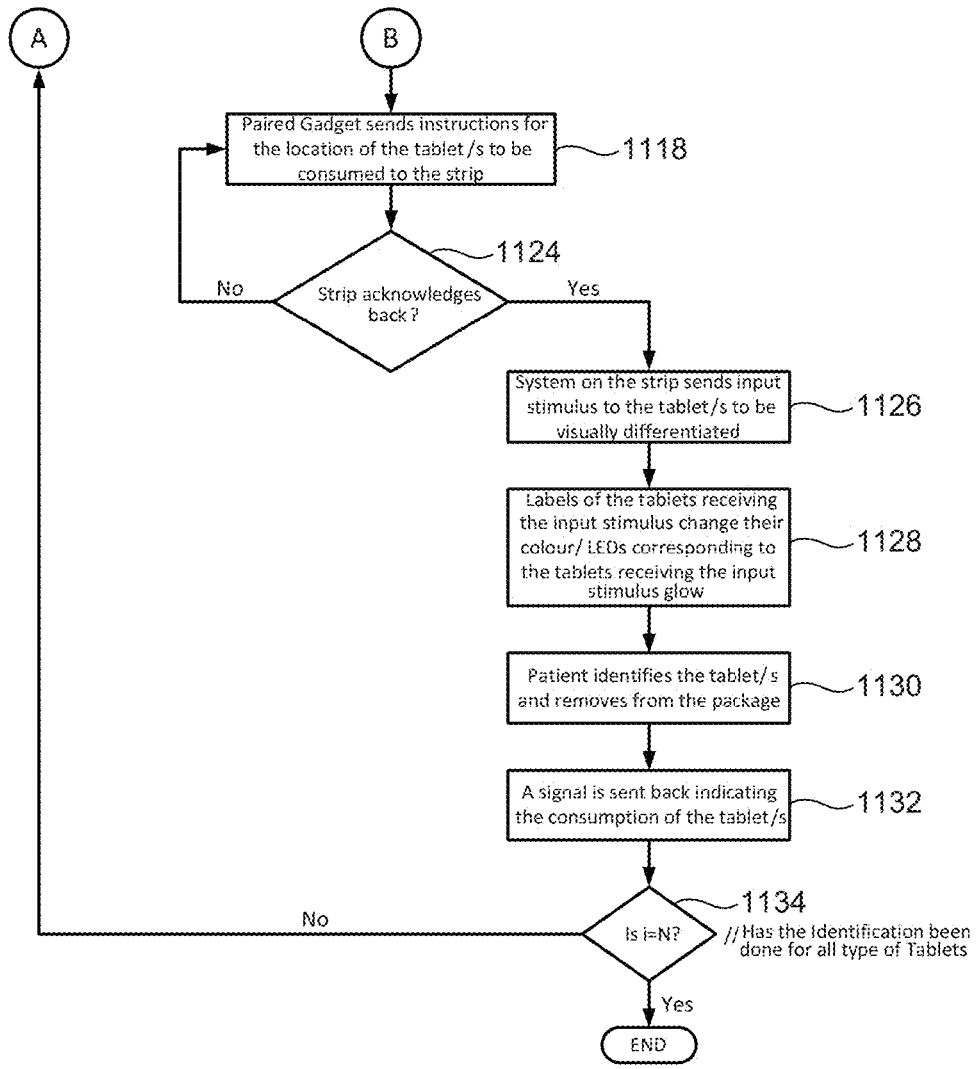

FIG. 11A through FIG. 11B is a flow diagram illustrating a method of using the medicine strip and the individual sections containing the corresponding tablets of FIG. 1 with the paired gadget 702 of FIG. 7 according to an embodiment herein. In step 1102, the client application software residing on the paired gadget 702 keeps running a timer which intimates at a time instant for consumption of one or more tablets of each type. In step 1104, variables are initialized (i.e. 'i' is set to zero (i=0), and 'i' is incremented by 1 (i=i+1) which indicates identification of next type of tablets). In step 1106, it is checked whether is it a time to consume a tablet of type 'i'? If it is the time to consume a tablet of type 'i', then the unique ID of the medicine strip containing the tablets of type 'i' is identified in step 1108. Else (if No), the step 1104 is repeated by incrementing the value of 'i' by 1.

In step 1110, connection is initialized between the medicine strip and the paired gadget 702. In step 1112, the medicine strip is polled using its unique ID. In step 1114, a wait time is initiated for the medicine strip to respond. In step 1116, it is checked whether the medicine strip acknowledges by transmitting the unique ID. If the medicine strip acknowledges by transmitting the unique ID, then the paired gadget 702 sends instructions to the section of the medicine strip corresponding to a particular tablet that needs to be consumed in step 1118.

Else (if No), then an error message is displayed on the paired gadget 702 (e.g., the mobile communication device) to bring the paired gadget 702 in close proximity of the medicine strip in step 1120. Then the user prompts for re-establishing the connection with the medicine strip in step 1122 and the step 1110 is repeated, or else, he/she may skip connection with the medicine strip and step 1104 is repeated by incrementing the value of 'i' by 1 for identifying the next type of tablets.

In step 1124, it is checked whether the medicine strip acknowledges to the instructions sent by the paired gadget 702. If the medicine strip acknowledges to the instructions sent by the paired gadget 702, the medicine identifier circuit 102 sends an electronic stimulus to a first section on the medicine strip to visually differentiate from other sections on the medicine strip in step 1126. Else (if No), then step 1118 is repeated. In step 1128, the first section on the medicine strip that receives the electronic stimulus changes its color/LED corresponding to the tablet receiving the input stimulus glow.

In step 1130, the patient identifies the appropriate tablet based on the input stimulus glow and removes the tablet from the corresponding section of the medicine strip. In step 1132, a signal is sent back indicating consumption of the tablet. In step 1134, it is checked whether "i=N" (i.e., identification done for all the types of tablets?). If "i=N" (if identification is done for all the types of tablets), then the process exits. Else, (if No) then step 1104 is repeated by incrementing the value of 'i' by 1 and performing the subsequent steps again.

Figure 12:
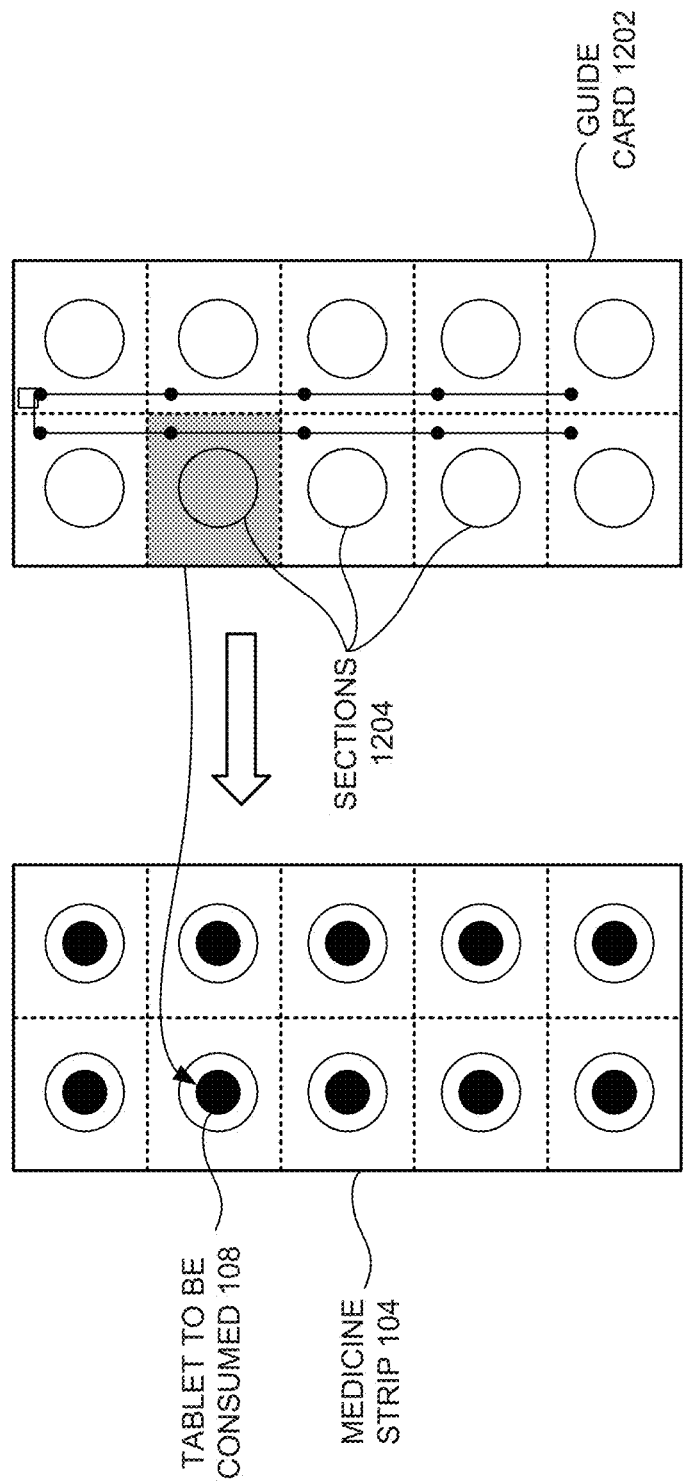
FIG. 12 illustrates a method of identifying the tablet to be consumed from a section within the medicine strip of FIG. 1 using a guide card according to an embodiment herein.

FIG. 12 illustrates a method of identifying the tablet to be consumed from a section within the medicine strip 104 of FIG. 1 using a guide card 1202 according to an embodiment herein. As an alternative to the medicine identifier circuit 102 on the medicine strip 102, this can also be embedded on the guide card. This guide card 1202 is essentially a footprint of the representative medicine strip 104 and provides the functionality of identifying the right tablet(s). The guide card 1202 does not contain the tablets. This guide card 1202 will be programmed by the retailer as per the patient's prescription at the time of dispensing the medicines and will be attached to the corresponding medicine strips. The guide card 1202 can be handed over to the patient along with the normal medicine strip.

The only difference is that the guide card 1202 is used in place of the medicine strip itself. The guide card 1202 includes the medicine identifier circuit 102, and one or more sections 1204. At the time of dispensing the medicine, the retailer programs the guide card 1202 or the paired gadget 702 and physically attaches one or more medicine strips of a particular type of medicine to its corresponding guide card. At an appropriate time a particular section 1204 on the guide card 1202 corresponding to the particular tablet to be consumed becomes visually distinguishable. The user uses this section 1204 of the guide card 1202 as a guide to identify the matching section and the corresponding predefined tablet on the medicine strip to consume the tablet at a predefine time.

Further, if a patient needs to consume fractional tablets, then a mechanism can be built to visually differentiate only half or quarter of a package signifying that half or quarter of the tablet needs to be consumed. For consumption of the medicines in the liquid form, the medicine identifier circuit 102 can be embedded on a sheet made of an appropriate material and can be pasted onto the bottles like a sticker. At the appropriate pre-programmed time to take the medicine, the medicine identifier circuit 102 visually differentiates the signs corresponding the amount to be consumed (½ or full spoon, etc.).

Figure 13A:
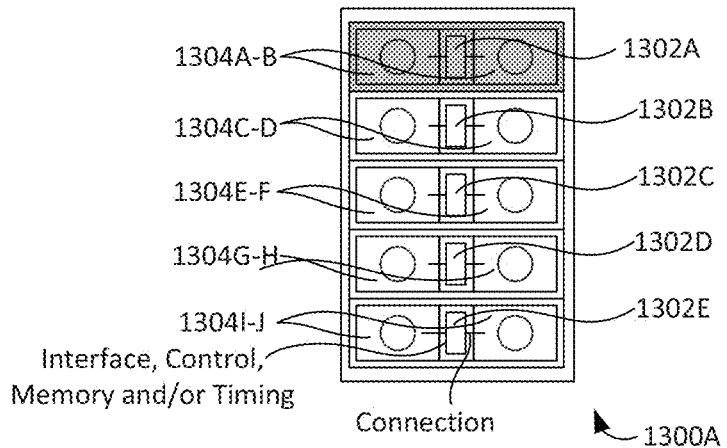
FIG. 13A illustrates a representation of the medicine strip having at least one programmable system, a plurality of sections, and a plurality of programmable sub-systems according to an embodiment herein.
Figure 13B:
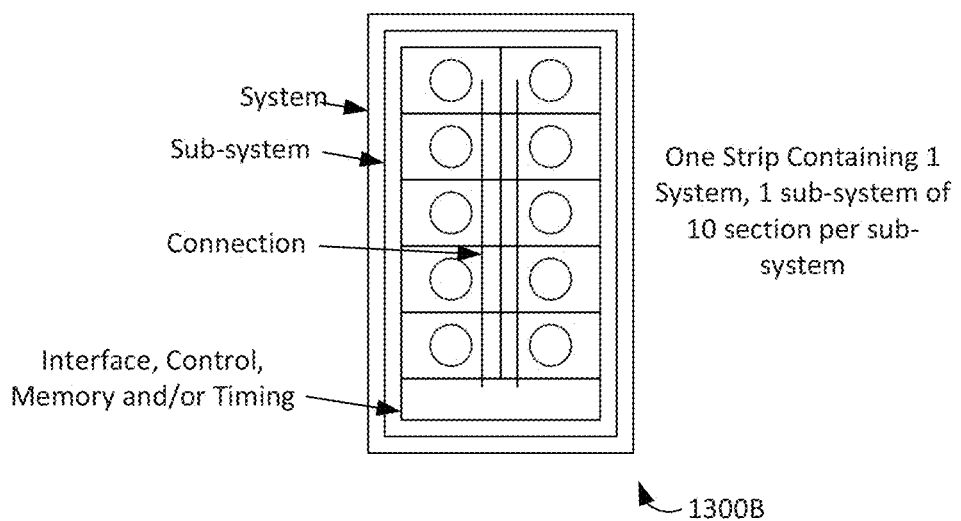
FIG. 13B illustrates a representation of the medicine strip having one programmable system, at least one programming sub-system having one or more sections per programmable sub-system.
Figure 13C:
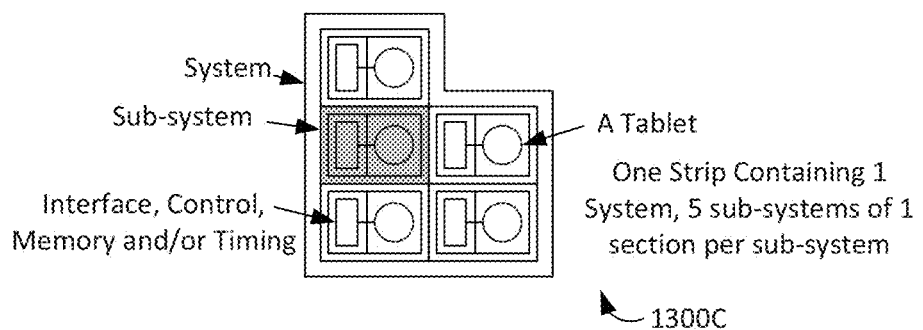
FIG. 13C illustrates a representation of the medicine strip having at least one programmable system, a plurality of programmable sub-systems, and a plurality of sections according to an embodiment herein.

FIG. 13A through FIG. 13C illustrates a representation of the medicine strip with a programmable system and a plurality of programmable sub-systems according to an embodiment herein. FIG. 13A illustrates a representation of the medicine strip having at least one programmable system, a plurality of sections 1304A-J, and a plurality of programmable sub-systems 1302A-E according to an embodiment herein. Each of the programmable sub-system correspond to each at least two 2 sections as shown in FIG. The programmable sub-system 1302A-E includes an interface, a controller, a memory, and a timer similar to the programmable medicine identifier circuit 104 of FIG. 1. FIG. 13B illustrates a representation of the medicine strip having one programmable system, at least one programming sub-system having one or more sections per programmable sub-system. FIG. 13C illustrates a representation of the medicine strip having at least one programmable system, a plurality of programmable sub-systems, and a plurality of sections according to an embodiment herein. Each of the programmable sub-systems corresponds to at least one section. Each of the sections corresponds to one tablet in a tablet strip.

In one embodiment, the programmable system further includes at least one programmable sub-system that includes at least one of a wired interface or a wireless interface coupled to the plurality of sub-sub-systems. The wired interface or the wireless interface receives a set of instructions that includes a set of sub-sections and their corresponding times from a programming device. The programmable sub-system further includes a memory that stores said set of instructions, a timer that tracks time and generates a message based on the set of instructions, a controller that controls at least one of a wired interface or a wireless interface, the memory and the timer, and generates an electrical stimulus and communicates the electrical stimulus to a first sub-section of the plurality of sub-sections at a first time based on the set of instructions. The first sub-section is modified visually at the first time in response to the electrical stimulus. Each of the at least one programmable sub-system corresponds to at least one sub-section.

Figure 14:
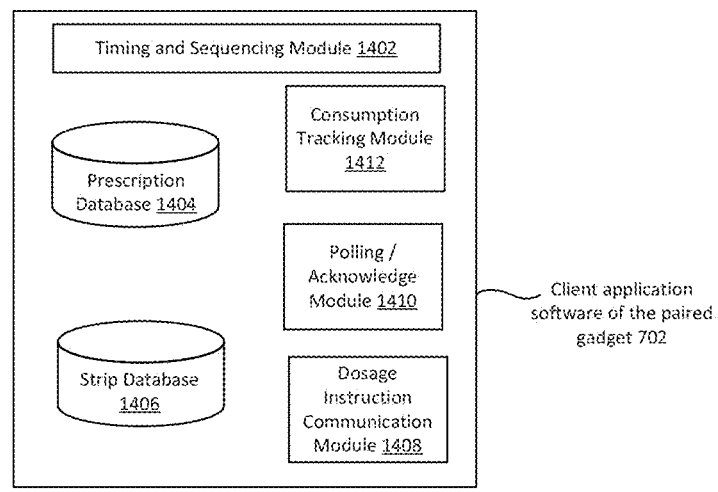
FIG. 14 illustrates an exploded view of the client application software of the paired gadget of FIG. 7 according to an embodiment herein.

FIG. 14 illustrates an exploded view of the client application software of the paired gadget 702 of FIG. 7 according to an embodiment herein. The client application software includes a timing and sequence module 1402, a prescription database 1404, a strip database 1406, an dosage instructions communication module 1408, a polling/acknowledge module 1410, and a consumption tracking module 1412. The timing and sequence module 1402 indicates a time of consumption for a medicine type to be consumed and retrieves an identifier of a programmable system corresponding the medicine type. The prescription database 1404 includes a medicine type information, a total number of tablets to be consumed, a timing information, and a dosage information, etc. The strip database 1406 includes a number of medicine strips information, a number of sub-system per medicine strip information, a number of tablets per sub-system information, and a sub-system ID information. The client application software may further include a validation module that processes a confirmation of a programmable system belonging to a medicine type based on an identifier received from the programmable system to validate the programmable system as a validated programmable system.

The dosage instructions communication module 1408 communicates said dosage information, for each the medicine type to the validated programmable system based on a user action. In one embodiment, the user action may be bringing the medicine strip in a close proximity to the programming device 112 or by giving a user input. The polling/acknowledge module 1410 polls for a medicine strip using a unique ID that corresponds to that particular medicine strip. Further the polling/acknowledge module 1410 checks if the medicine strip acknowledges to the instructions sent by the paired gadget 702. The consumption tracking module 1412 tracks the sections of the tablets that are consumed based on a signal that is sent back indicating the consumption of the tablet from the programmable sub-system. The client application software may further include a strip identification module that identifies a particular medicine strip for pairing with the paired gadget 702.

Figure 15:
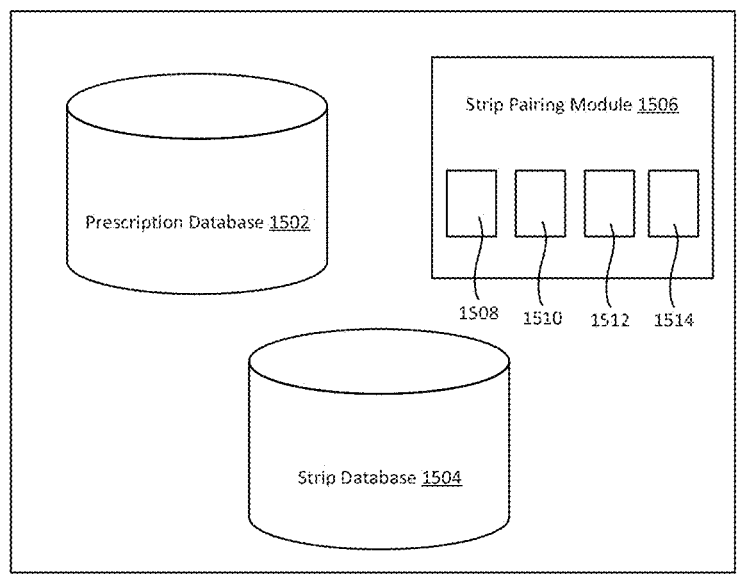
FIG. 15 is an exploded view of the programming device of FIG. 1 according to an embodiment herein.

FIG. 15 is an exploded view of the programming device 112 of FIG. 1 according to an embodiment herein. The programming device 112 includes a prescription database 1502, a strip database 1504, and a strip pairing module 1506. The strip pairing module 1506 includes a sequence module 1508, a strip validation module 1510, a polling/acknowledge module 1512, and an instructions communication module 1514. The prescription database includes at least one medicine type, a timing information, a dosage information, and a total number of tablets to be consumed for each the medicine type. The strip database 1504 is populated when a medicine strip is programmed with a prescription information. The strip pairing module 1506 processes the number of medicine strips that needs to be programmed for each the medicine type. The sequence module 1508 processes a number of programmable systems that needs to be programmed for each the medicine type. The strip validation module 1510 that processes a confirmation of a programmable system belonging to a medicine type based on an identifier received from the programmable system.

The polling/acknowledge module 1512 polls for a medicine strip using a unique ID that corresponds to that particular medicine strip. Further the polling/acknowledge module 1512 checks if the medicine strip acknowledges to the instructions sent by the paired gadget 702. The instructions communication module 1514 sends the medicine type, the timing information, the dosage information, and the total number of tablets to be consumed for each the medicine type to the programmable system.

FIG. 16 is a table view of the prescription database 1404 and the medicine strip database 1406 of FIG. 14 of the paired gadget 702 of FIG. 7 according to an embodiment herein. The prescription database 1402 includes a medicine type field 1602, a total number of tablets to be consumed field 1604, a timing information field 1606, and a dosage information field 1608. The strip database field 1406 includes a number of medicine strips field 1610, a number of sub-system per strip field 1612, a number of tablets per sub-system field 1614, and a sub-system ID field 1616. The medicine field 1602 includes one or more medicine names that are prescribed for the tablet consumption. For example, the medicine names may include Amox, Cetrizine, Crocin, Vitamin B, etc. The total number of tablets to be consumed field 1604 includes number of tablets to be consumed. For example, for the medicine Amox, the total number of tablets to be consumed are 10 no's. For the medicine Cetrizine, the total number of tablets to be consumed are 4 no's. For the medicine Crocin, the total number of tablets to be consumed are 9 no's. For the medicine Vitamin B, the total number of tablets to be consumed are 30 no's.

The timing information field 1606 includes timing information for a particular tablet to be consumed. For example, the medicine Amox should be consumed between 8.00 AM to 10.00 AM in the morning, and 8.00 PM to 10.00 PM in the night. Similarly, the medicine "Cetrizine" should be consumed between 8.00 AM to 10.00 AM in the morning. The medicine "Crocin" should be consumed between 8.00 AM to 10.00 AM in the morning, 2.00 PM to 4.00 PM in the afternoon, and 8.00 PM to 10.00 PM in the night. The medicine "Vitamin B" should be consumed between 8.00 PM to 10.00 PM in the night.

The dosage information field 1608 indicates the dosage information for a particular medicine to be consumed at a particular time. For example, 1 medicine Amox should be consumed between 8.00 AM to 10.00 AM in the morning, another dosage of the medicine Amox should be consumed between 8.00 PM to 10.00 PM in the night. Similarly, 1 medicine Cetrizine should be consumed between 8.00 AM to 10.00 AM in the morning. 1 medicine Crocin should be consumed between 8.00 AM to 10.00 AM in the morning. A second dosage of the medicine Crocin should be consumed between 2.00 PM to 4.00 PM in the afternoon, and a third dosage of the medicine Crocin should be consumed between 8.00 PM to 10.00 PM in the night. Similarly, half (½) dosage of the medicine Vitamin B should be consumed between 8.00 PM to 10.00 PM in the night.

The number of strips field 1610 includes the total number of strips for each of the medicine type. For example, for the medicine type Amox, it is 1 medicine strip, for Cetrizine it is 1 medicine strip, for Crocin it is 1 medicine strip, and for Vitamin B, it is 3 medicine strip. The number of sub-system per strip field 1612 includes the number of sub-system within a medicine strip. For example, the medicine strip Amox includes 1 sub-system, the medicine strip Cetrizine includes 4 subsystem, the medicine strip Crocin includes 1 sub-system, and the medicine strip Vitamin B includes 1 sub-system.

The number of tablets per sub-system field 1614 indicates the tablets present in one sub-system. For example, there are 10 tablets in the sub-system for the medicine type Amox, there is 1 tablet in the sub-system for the medicine type Cetrizine, there are 10 tablets in the sub-system for the medicine type Crocin, and there are 10 tablets in the sub-system for the medicine type Vitamin B. The sub-system ID field 1616 includes a medicine strip ID corresponding to the medicine type for each medicine strip. For example, the sub-system ID for the medicine strip Amox is AAA1, the sub-system IDs for the medicine strips Cetrizine are BBB1, BBB2, BBB3, and BBB4, etc. The sub-system ID for the medicine strip Crocin is CCC1, and the sub-system IDs for the medicine strips Vitamin B are DDD1, CCC2, and CCC3.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 17:
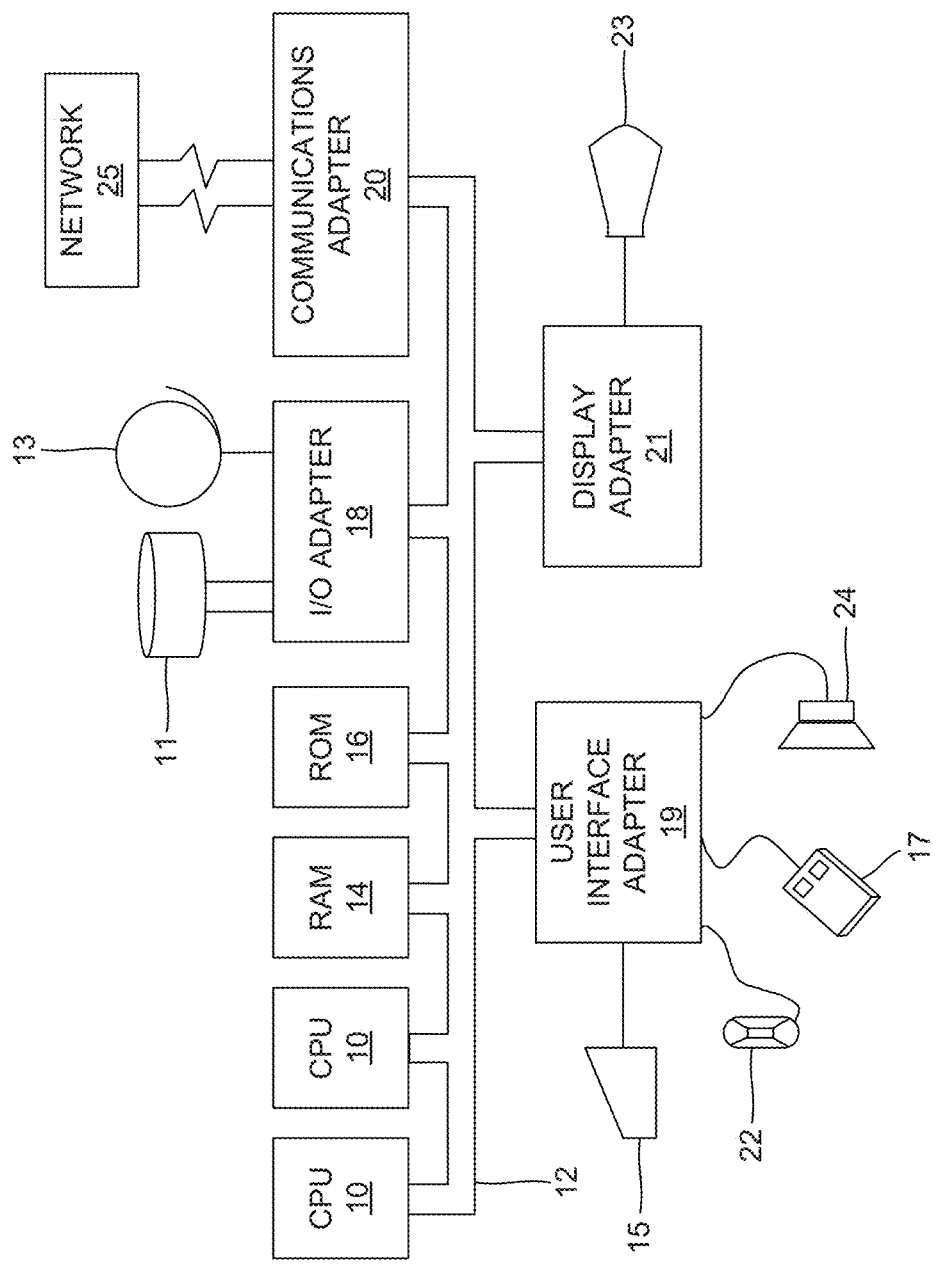
FIG. 17 illustrates a schematic diagram of a computer architecture according to an embodiment herein.

A representative hardware environment for practicing the embodiments herein is depicted in FIG. 17. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

Figure 18:
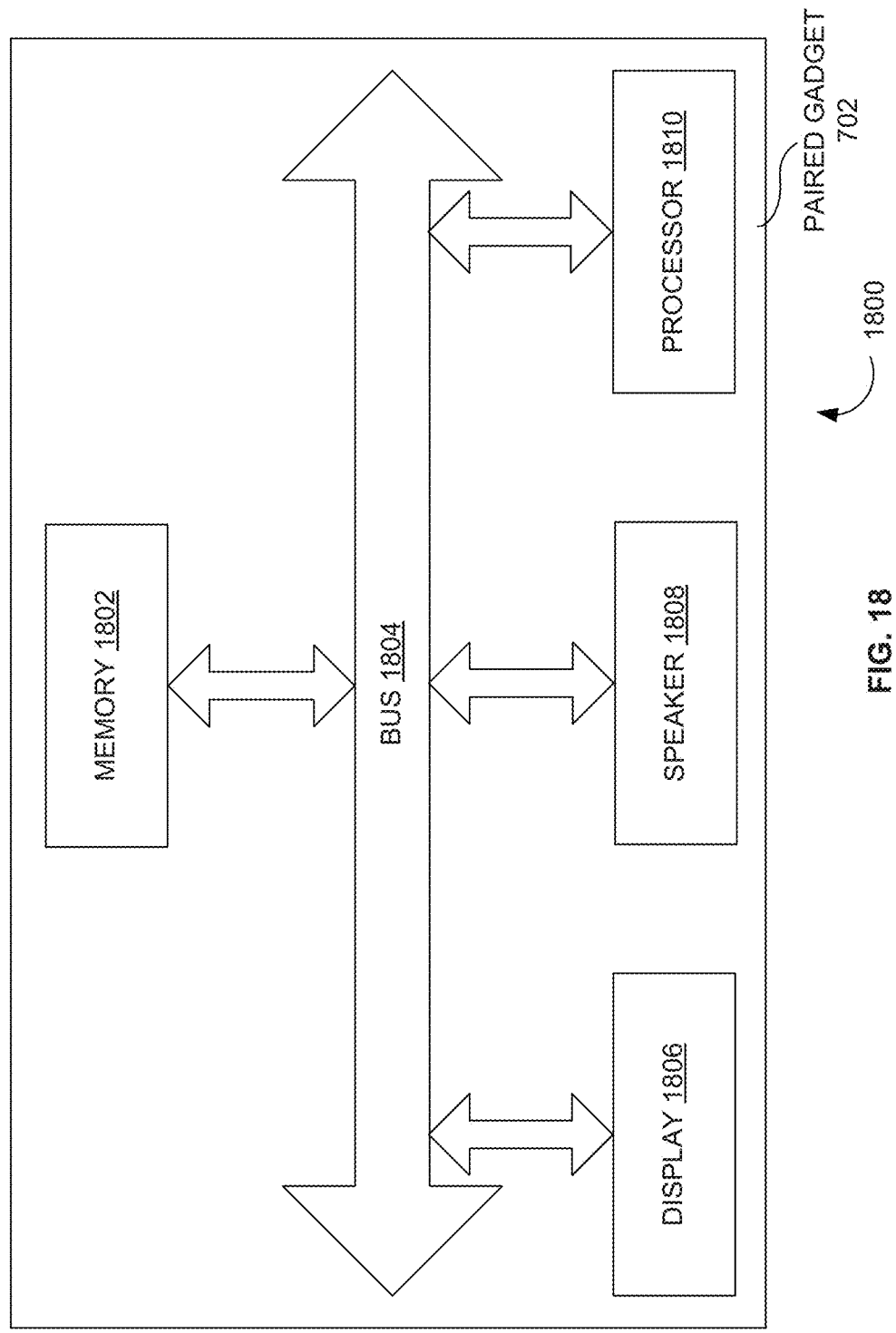
FIG. 18 illustrates exploded view of a typical paired gadget having a memory having a computer set of instructions, a bus, a display, a speaker, and a processor capable of processing a set of instructions to perform any one or more of the methodologies according to an embodiment herein.

FIG. 18 illustrates exploded view 1800 of a typical paired gadget (e.g., the paired gadget 702 of FIG. 7) having an a memory 1802 having a computer set of instructions, a bus 1804, a display 1806, a speaker 1808, and a processor 1810 capable of processing a set of instructions to perform any one or more of the methodologies according to an embodiment herein. In one embodiment, the paired gadget 702 is a mobile communication device. The processor 1810 may also enable digital content to be consumed in the form of video for output via one or more displays 1806 or audio for output via speaker and/or earphones 1808. The processor 1810 may also carry out the methods described herein and in accordance with the embodiments herein. Digital content may also be stored in the memory 1802 for future processing or consumption. The memory 1802 may also store program specific information and/or service information (PSI/SI), including information about digital content available in the future or stored from the past.

A user of the paired gadget 702 may view this stored information on display 1806 and select an item of for viewing, listening, or other uses via input, which may take the form of keypad, scroll, or other input device(s) or combinations thereof. When digital content is selected, the processor 1810 may pass information. The content and PSI/SI may be passed among functions within the paired gadget 702 using bus 1804.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A programmable system embedded in a guide card to visually indicate a predefined tablet to be consumed at a predefined time, said programmable system comprising:
   a plurality of sections each corresponding to one of a plurality of tablets in a tablet strip, wherein said guide card is separate from said tablet strip;
   at least one of a wired interface or a wireless interface coupled to said plurality of sections, wherein said at least one of said wired interface or said wireless interface receives a set of instructions that comprise a set of sections and their corresponding times from a programming device;
   a memory that stores said set of instructions;
   a timer that tracks time and generates a message based on said set of instructions; and
   a controller that controls said at least one of a wired interface or a wireless interface, said memory and said timer, generates an electrical stimulus and communicates said electrical stimulus to a first section of said plurality of sections at a first time based on said set of instructions, wherein said first section is modified visually at said first time in response to said electrical stimulus.

2. The programmable system of claim 1, wherein said guide card does not contain tablets, wherein said guide card comprises a medicine identifier circuit, and wherein said medicine identifier circuit is configured to enable at least one section of said guide card to be modified visually to indicate said predefined tablet to be consumed at said predefined time.

3. The programmable system of claim 1, wherein said first section is partially modified visually in proportion to a dosage information corresponding to said first section.

4. A programming device for programming a paired gadget that sends a set of instructions to a medicine identifier circuit embedded within a medicine strip, wherein said medicine strip comprises a set of sections and their corresponding times, wherein said paired gadget comprises a processor, an input means, a display means, and a memory, wherein said instructions execute a method comprising:
   obtaining a medicine prescription for each of a plurality of types of tablets, wherein said medicine prescription comprises a timing information and a dosage information for each of said types of tablets;

pairing a plurality of medicine strips for said types of tablets with said paired gadget, wherein each of said medicine strips comprises a unique ID, wherein each of said medicine strip sends said unique ID to said paired gadget;

displaying, by said display means, each of said unique ID of said medicine strips, on said paired gadget;

validating said displayed unique ID with a unique ID that is printed on said medicine strip;

programming said paired gadget with said medicine prescription comprising said timing and said dosage information for each of said 'N' type of tablets on said unique ID being validated;

initiating a connection by said paired gadget with at least one of said paired plurality of medicine strips based on said timing and dosage information, said at least one of said paired plurality of medicine strips being in a vicinity of said paired gadget; and sending said instructions to said medicine identifier of said medicine strip circuit through said connection, wherein said instructions trigger communication of an electronic stimulus to a first section of said sections of said medicine strip at a first time, wherein said first section is modified visually at said first time in response to said electrical stimulus that corresponds to a predefined tablet to be consumed at a predefined time from said medicine strip.

5. The programming device of claim 4, wherein said medicine prescription is at least one of an electronic format, or a word processing format.

6. A programmable system associated with a tablet strip, to visually indicate a predefined tablet to be consumed at a predefined time, said programmable system comprising:

two or more programmable sub-systems, wherein each of said two or more programmable sub-systems correspond to at least one tablet in said tablet strip, and wherein each of said two or more programmable sub-systems comprises:

at least one of a wired interface or a wireless interface that receives a set of instructions that comprise a corresponding time of said programmable sub-system from a programming device;

a memory that stores said set of instructions;

a timer that tracks time and generates a message based on said set of instructions; and a controller that controls said at least one of said wired interface or said wireless interface, said memory and said timer, generates an electrical stimulus and communicates said electrical stimulus to said programmable sub-system at a first time based on said set of instructions, wherein said programmable sub-system is modified visually at said first time in response to said electrical stimulus, wherein said programmable sub-system is embedded within a guide card that is separate from said tablet strip, wherein said guide card does not contain tablets.

7. The programmable system of claim 6, wherein said two or more programmable sub-systems are partially modified visually in proportion to a dosage information corresponding to said two or more programmable sub-systems.

* * * * *